United States Patent [19]

Davenport et al.

[11] Patent Number: 4,524,217

[45] Date of Patent: Jun. 18, 1985

[54] PROCESS FOR PRODUCING N-ACYL-HYDROXY AROMATIC AMINES

[75] Inventors: Kenneth G. Davenport; Charles B. Hilton, both of Corpus Christi, Tex.

[73] Assignee: Celanese Corporation, New York, N.Y.

[21] Appl. No.: 618,659

[22] Filed: Jun. 8, 1984

[51] Int. Cl.$^3$ .................. C07C 103/12; C07C 103/22
[52] U.S. Cl. .................................................. 564/223
[58] Field of Search ........................................ 564/223

[56] References Cited

U.S. PATENT DOCUMENTS

| | | | |
|---|---|---|---|
| 2,833,825 | 5/1978 | Lewis | 260/592 |
| 3,192,213 | 6/1965 | Krapcho | 564/223 X |
| 3,201,401 | 8/1965 | Krapcho | 564/223 X |
| 3,235,456 | 2/1966 | Thominet et al. | 564/223 X |
| 3,389,171 | 6/1968 | White et al. | 564/223 X |
| 3,413,340 | 11/1968 | Wallingford | 564/223 X |
| 3,492,349 | 1/1970 | Doyle et al. | 564/223 |
| 3,555,091 | 1/1971 | Alain et al. | 564/223 X |
| 3,775,485 | 11/1973 | Pilgram et al. | 564/223 X |
| 3,786,090 | 1/1974 | Hussain | 564/223 |
| 3,801,644 | 4/1974 | von Strandtmann et al. | 564/223 X |
| 3,839,446 | 10/1974 | Teach | 564/223 X |

FOREIGN PATENT DOCUMENTS 2616986  10/1977  Fed. Rep. of Germany ...... 564/223

OTHER PUBLICATIONS

Simons et al., J. Amer. Chem. Soc., 62, 485 and 486 (1940).
Dann and Mylius, Annalen der Chemie, 587 Band, 1–15, (W. Germany, 1954)—English translation provided.
Simons et al., J. Amer. Chem. Soc., 61, 1795 and 1796 (1939).
Auwers et al., Chemishe Berichte, 58, 36–51 (Germany 1925)—English translation provided.
Ganboa et al., Synthetic Communications, 13 (11) 941–944 (1983).
Pearson et al., J. Amer. Chem. Soc., 75, 5905–5908 (1953).

*Primary Examiner*—Paul F. Shaver
*Attorney, Agent, or Firm*—M. Turken; D. R. Cassady

[57] ABSTRACT

N-acyl-hydroxy aromatic amines, e.g. N-acetyl-para-aminophenol (APAP), are prepared by reacting a hydroxy aromatic ketone, e.g. 4-hydroxyacetophenone, with a hydroxylamine salt and a base to obtain the ketoxime of the ketone, e.g. 4-hydroxyacetophenone oxime, and then subjecting the ketoxime to a Beckmann rearrangement in the presence of a catalyst to form the N-acyl-hydroxy aromatic amine.

6 Claims, No Drawings

PROCESS FOR PRODUCING N-ACYL-HYDROXY AROMATIC AMINES

This invention relates to the production of N-acylhydroxy aromatic amines, e.g. N-acetyl-para-aminophenol (APAP) from hydroxy aromatic ketones e.g. 4-hydroxyacetophenone.

BACKGROUND OF THE INVENTION

It is known to prepare N-acyl-hydroxy aromatic amines, e.g. N-acetyl-para-aminophenol (APAP), by acylating the corresponding hydroxy aromatic amine, e.g. para-aminophenol, with an acetylating agent such as an anhydride, e.g. acetic anhydride. However this reaction may cause problems such as the difficulty of mono-acetylating the amine group, oligomerization of the hydroxy aromatic amine, and color body formation. Nonetheless, the APAP made by this reaction is an important commodity of commerce, being one of the most widely used over-the-counter analgesics.

The preparation of hydroxy aromatic ketones by the Fries rearrangment of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15 (1954), show the rearrangement of phenyl acetate in hydrogen fluoride to 4-hydroxyacetophenone, with a maximum yield of 81% after 24 hours of reaction time, and report a yield of 92% stated to be obtained by K. Weichert as reported in Angewandte Chemie 56, 338 (1943). However, Dann and Mylius suggest that the difference in yields may be at least partly due to the previous ignoring by Weichert of the accompanying 2-hydroxyacetophenone.

Dann and Mylius also disclose the reaction of phenol and glacial acetic acid in the presence of hydrogen fluoride to produce 4-hydroxyacetophenone at a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone in 40% yield.

Meussdoerffer et al, German Offenlegungsschrift No. 26 16 986 published Oct. 27, 1977 and assigned to Bayer AG, disclose the acylation of phenolic compounds such as phenol itself with an acyl halide such as acetyl chloride to form hydroxy aromatic ketones.

Auwers et al, Chemische Berichte, 58, 36–51, (1925) show the Beckmann rearrangement of a large number of oximes of aromatic ketones most of which are substituted acetophenones. However, the only attempted rearrangement of the oxime of a ring-unsubstituted hydroxy aromatic ketone was that of the oxime of o-hydroxyacetophenone, but no amine was formed, i.e. the attempted rearrangement was unsuccessful; see page 41.

Ganboa et al, Synthetic Communications 13(11), 941–944 (1983) show the production of acetanilide from acetophenone by refluxing in a solution of hydroxylamine hydrochloride. There is however no suggestion of the synthesis of N-acyl hydroxy aromatic amines such as N-acetyl-para-aminophenol (APAP).

Pearson et al, Journal of the American Chemical Society 75 5905–5908 (Dec. 5, 1953) disclose the formation of hydrazones from ketones by reaction with hydrazine hydrate and the rearrangement of the hydrazone to the amide by reaction with sodium nitrite and concentrated sulfuric acid. Specifically, on page 5907 Pearson et al show the rearrangement of p-hydroxyacetophenone hydrazone to p-hydroxyacetanilide, i.e., APAP.

SUMMARY OF THE INVENTION

In accordance with one aspect of this invention, N-acyl-hydroxy aromatic amines, e.g. N-acetyl-para-aminophenol (APAP), are produced by reacting a hydroxy aromatic ketone, e.g. 4-hydroxyacetophenone (4-HAP), with a hydroxylamine salt, to form the ketoxime of the ketone and subjecting the ketoxime to a Beckmann rearrangement in the presence of a catalyst to form the N-acyl-hydroxy aromatic amine.

The ketoxime formation of this invention proceeds as indicated in equation (I):

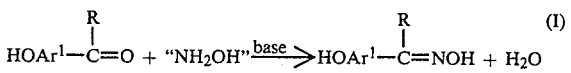

When APAP is the desired product the ketoxime formation proceeds as in equation (II):

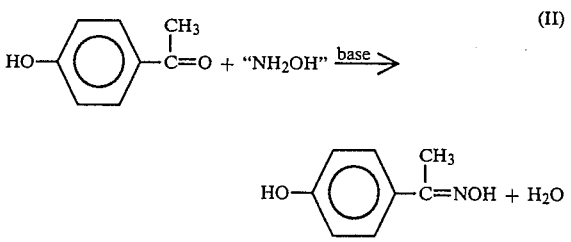

The Beckmann rearrangement of this invention proceeds as in equation (III):

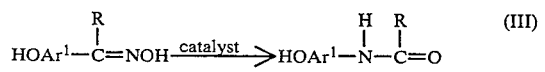

while the Beckmann rearrangement when APAP is the desired product proceeds as in equation (IV):

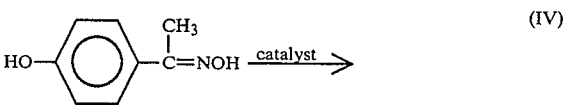

-continued

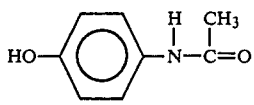

In equations I and III, $Ar^1$ is a divalent aromatic radical. The specific nature of the radical is not critical but it is preferably a radical resulting from the removal of two hydrogen atoms from benzene, naphthalene, or biphenyl, either unsubstituted or with ring hydrogens substituted with radicals such as alkyl, alkenyl, alkynyl, alkoxy or acyloxy containing 1 to 18 carbon atoms, aralkyl containing 7 to 18 carbon atoms; halogen, e.g. chlorine, bromine, or iodine; hydroxy; amino; or sulfhydryl. $Ar^1$ is preferably 1,4-phenylene, 2,1-naphthylene, 2,6-naphthylene, 5-phenyl-1,2-phenylene, 3-phenyl-1,4-phenylene or 3-methyl-1,4-phenylene with the ketocarbon and corresponding groups occupying the first stated numbered position of $Ar^1$ when the position are not equivalent. Most preferably $Ar^1$ is 1,4-phenylene.

R in the foregoing equations is a monovalent organic radical containing, for example, 1 to 18 carbon atoms preferably 1 to 4 carbon atoms. R may be, for example, alkyl, alkenyl, alkynyl, alkoxy, acyl or acyloxy containing 1 to 18 carbon atoms, either unsubstituted or substituted with radicals such as halogen, e.g. chlorine, bromine, or iodine; hydroxy; amino; sulfhydryl; or an aryl radical, Ar which may be a monovalent radical corresponding to the definition of $Ar^1$ given above except that the carbon bonded to OH is bonded to a hydrogen instead. More preferably, R is methyl, ethyl, propyl, or n-butyl and most preferably methyl corresponding to the use of acetate esters and methyl ketones in equations (I) and (III). The preferred specific hydroxy aromatic ketone used to form the oxime is 4-hydroxyacetophenone (4-HAP) and the preferred product is N-acetyl-para-aminophenol (APAP).

The hydroxy aromatic ketone used to form the oxime may be prepared by any method known in the art. For example, it may be prepared by the Fries rearrangement of the corresponding aromatic ester as indicated by the following equation where Ar, $Ar^1$ and R have the definitions given above:

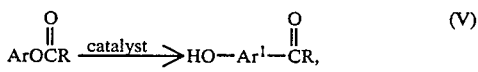

(V)

Alternatively, a phenolic compound and an acylating agent may be reacted in a Friedel-Crafts acylation to form the hydroxy aromatic ketone, in accordance with the following equation:

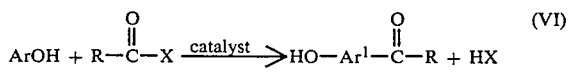

(VI)

where Ar, $Ar^1$ and R have the meanings given previously and X is the residue minus the acyl group,

of the compounds which are known acylating agents, such as hydroxy, acyloxy e.g. acetoxy, and halide, e.g. fluoride, chloride, bromide, and iodide. Examples of phenolic compounds which may be employed are phenol, 1-naphthol, 2-naphthol, 2-phenylphenol, 4-phenylphenol and o-cresol. Acylating agents which may be used are for example alkanoic acids, e.g. acetic and propionic acids, alkanoic acid anhydrides, e.g. acetic and propionic anhydrides, and acyl halides, e.g. acetyl and propionyl chlorides and bromides. Note that although the reaction of a phenolic compound and an acylating agent is characterized herein as a "Friedel-Crafts acylation", no opinion as to the mechanism of reaction should be implied by this characterization.

The catalyst for both of the foregoing reactions is preferably hydrogen fluoride but any other catalyst known in the art to be effective for the Fries and Friedel-Crafts reactions may be used, e.g. aluminum chloride, zinc chloride, or boron trifluoride.

In carrying out the reaction, the aromatic ester or phenolic compound and acylating agent, catalyst and if desired when an aromatic ester is the starting material, an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at a pressure, for example, of about 50 to about 500 psia. If HF is used as the catalyst it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 60 moles per mole of aromatic ester or phenolic compound initially present in the reaction zone. If APAP is the desired product of the reaction, the starting material if a Fries rearrangement is employed will be phenyl acetate while phenol and an acetylating agent such as acetic acid is the starting material if a Friedel-Crafts acylation is utilized. In both cases, the starting material is converted to 4-HAP which is in turn converted by the process of this invention to APAP.

The conversion of hydroxy aromatic ketones, e.g., 4-HAP, into N-acyl-hydroxy aromatic amines, e.g., APAP, is accomplished by first forming the ketoxime from the hydroxy aromatic ketone as indicated by equations (I) and (II), by contacting the ketone with a hydroxylamine salt, e.g. hydroxylamine hydrochloride, hydroxylamine sulfate, hydroxylamine bisulfate, or hydroxylamine phosphate, and a base, e.g. ammonium hydroxide, potassium hydroxide, sodium hydroxide, or lithium hydroxide in an amount, for example, for 1 to 3 moles per mole of hydroxylamine, at a temperature, for example of 0° to 60° C. for a period, for example, of 1 to 4 hours. Any pressure may be used, e.g., 80 mm. of mercury to 10 atmospheres absolute. The reaction is preferably carried out in an aqueous or alcoholic medium, i.e., in the presence of water and/or an alcohol such as methanol, ethanol, or isopropanol.

The ketoxime is converted into the corresponding N-acyl-hydroxy aromatic amine by a Beckmann rearrangement as shown in equations (III) and (IV), by contacting the ketoxime with a catalyst for the reaction at a temperature, for example of 0° to 118° C. for a period for example of 1 to 4 hours. The pressure is not critical and may be, for example, in the range of 80 mm. of mercury to 10 atmospheres absolute. Any Beckmann rearrangement catalyst may be used, as for example, an acid, e.g. mineral acid such as sulfuric or hydrochloric acid, an organic acid such as trifluoroacetic acid, paratoluenesulfonic acid, benzenesulfonic acid or methanesulfonic acid, an acidic ion-exchange resin such as Amberlyst 15 or Nafion 501 which are sulfonic acid ion-exchange resins, or thionyl chloride in liquid sulfur dioxide. The reaction may be advantageously carried out in the presence of the glacial carboxylic acid corresponding to the N-acyl group of the desired product which will ordinarily yield the hydroxy derivative. The total amount of glacial carboxylic acid is not critical but is usually present such that the ketoxime concentration is in the range of 2 to 50% by weight at the start of the reaction.

The following examples further illustrate the invention.

EXAMPLE 1

This example illustrates the preparation of 4-hydroxyacetophenone by the Fries rearrangement of phenyl acetate using hydrogen fluoride as catalyst with acetic anhydride as additive.

To a 300 cc Hastelloy C autoclave were added 30.6 grams (0.3 mole) of acetic anhydride. The autoclave was cooled to $-50°$ C. and evacuated to 5 Torr whereupon 120 g (6.0 mole) of anhydrous hydrogen fluoride was transferred from a cylinder to the autoclave. After the transfer of hydrogen fluoride was completed, the internal temperature and the internal pressure of the autoclave was adjusted to $-50°$ C. and 0 psig using nitrogen, respectively. To the stirred autoclave was added 81.6 g (0.6 mol) of phenyl acetate at such a rate that the temperature of the mixture did not exceed $-23°$ C. Upon completion of phenyl acetate addition, the contents were warmed to 50° C. and stirred for 3 h during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using 45% potassium hydroxide and the mixture was then extracted with 75 ml of ethyl acetate (3×). The organic solution was dried over anhydrous magnesium sulfate, filtered, and the solvent was removed using a rotary evaporator.

The reaction proceeded with 98.1% conversion of phenyl acetate and with the following selectivities: phenol 1%; 4-hydroxyacetophenone (4-HAP) 82.3%; 2-hydroxyacetophenone (2-HAP) 4.3%; 3-hydroxyacetophenone (3-HAP) 0.1%; 4-acetoxyacetophenone (4-AAP) 3.8%; and 4-(4'-hydroxyphenyl)-acetophenone (HPAP) 0.4%.

EXAMPLE 2

This example describes the formation of 4-hydroxyacetophenone by the Fries rearrangement of phenyl acetate using hydrogen fluoride as catalyst and acetic acid as additive.

The procedure for Example 1 was repeated except that 18 grams (0.3 mole) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP 0; 2-HAP 5.8%; 4-AAP 0.3%; and HPAP 0.3%.

EXAMPLE 3

This example illustrates the preparation of 4-hydroxyacetophenone (4-HAP) by the Friedel-Crafts acetylation of phenol with acetic acid as the acetylating agent.

Phenol (9.4 g, 0.1 moles) and acetic acid (12.0 g, 0.2 moles) were charged to a 300 ml Hastelloy C autoclave at room temperature. The reactor was evacuated and cooled to $-20°$ C. HF (100 g, 5 moles) was then transferred into the reactor. The reactor was heated to 80° C. and maintained for 1 hour at reaction temperature. At the end of the reaction the reactor was cooled to 20° C. and the excess HF was vented to a KOH scrubber. Ethyl acetate was added to the contents of the reactor. The mixture was then neutralized with 45% aqueous KOH. The resulting organic phase was separated, dried over $MgSO_4$ and evaporated to afford a yellow solid which contained 13.1 g (0.096 moles) of 4-HAP.

EXAMPLE 4

This example illustrates the formation of 4-hydroxyacetophenone oxime from 4-hydroxyacetophenone and hydroxylamine hydrochloride.

A solution was prepared by adding 13.6 g (0.1 mol) of 4-hydroxyacetophenone, 7.6 g (0.11 mol) of hydroxylamine hydrochloride, and 10 g of water to 40 mL of ethanol. To the solution was added 5.0 g of 30% ammonium hydroxide which was then heated at reflux for 2 h. The ethanol was removed on a rotary evaporator to yield a yellow oil. An extractive work-up afforded 15.1 g (99%) of 4-hydroxyacetophenone oxime.

EXAMPLE 5

This example illustrates the formation of 4-hydroxyacetophenone oxime from 4-hydroxyacetophenone and hydroxylamine sulfate.

A solution was prepared by adding 20.4 g (0.15 mol) of 4-hydroxyacetophenone and 13.0 g (0.08 mol) of hydroxylamine sulfate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 6

This example illustrates the formation of 4-hydroxyacetophenone oxime from 4-hydroxyacetophenone and hydroxylamine phosphate.

A solution was prepared by adding 20.4 g (0.15 mol) of 4-hydroxyacetophenone and 12.9 g (65.6 mmol) of hydroxylamine phosphate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 7

This example illustrates the formation of N-acetyl-para-aminophenol by the Beckmann rearrangement of 4-hydroxyacetophenone oxime using an acidic ion-exchange resin as catalyst.

A mixture of 3.0 g of Amberlyst 15, (a sulfonic acid ion-exchange resin made by Rohm & Haas), 3.0 g (22.0 mmol) of 4-hydroxyacetophenone oxime, and 50 mL of acetic acid was heated at reflux under nitrogen for 2 h. The ion exchange resin was then removed and the acetic acid was distilled in vacuo to afford an orange residue. The residue was dissolved in ethanol and treated with activated carbon and anhydrous magnesium sulfate. Removal of the ethanol using a rotary evaporator produced 2.9 of a yellow oil, which upon drying afforded 2.0 g (66.7%) of N-acetyl-para-aminophenol.

EXAMPLE 8

This example illustrates the formation of N-acetyl-para-aminophenol by the Beckmann rearrangement of 4-hydroxyacetophenone oxime using trifluoroacetic acid as catalyst.

A solution of 10 g (66.2 mmol) of 4-hydroxyacetophenone oxime and 75 g of trifluoroacetic acid was heated at reflux under a nitrogen atmosphere. The trifluoroacetic acid was then removed in a rotary evaporator to afford 14.7 g of oil which was dissolved in 100 mL of water. Upon cooling to 0° C. for 0.5 h, crystallization occurred. Filtration and drying of the crystals yielded 7.1 g (71%) of N-acetyl-para-aminophenol.

EXAMPLE 9

This example illustrates the formation of N-acetyl-para-aminophenol by the Beckmann rearrangement of 4-hydroxyacetophenone oxime using thionyl chloride in liquid sulfur dioxide as catalyst.

A pressure bottle (cooled in a $CO_2$/acetone bath) was charged with 50 mL of $SO_2$, 0.05 mL of $SOCL_2$, and 15 g of 4-hydroxyacetophenone oxime. The $CO_2$/acetone bath was removed and the contents of the pressure bottle stirred for 1.5 h at room temperature. The $SO_2$ was then vented and the crystals washed from the pressure bottle with 50 mL of warm water. The pH of the aqueous slurry was adjusted to 6.5 by dropwise addition of 30% $NH_4OH$. The slurry was cooled in an ice bath and then filtered. The filtered crystals were washed with 10 mL of ice water and dried overnight in a vacuum oven (60° C./100 mm Hg) yielding 13.3 g (88.7%) of white crystals of N-acetyl-para-aminophenol having a melting point of 166.5°–170° C.

The procedures of the examples may also be used to prepare N-acetyl-(4-hydroxy-3-methylphenyl) amine from o-cresyl acetate or o-cresol and acetic acid; N-propionyl-para-aminophenol from phenyl propionate or phenol and propionic acid; and N-n-butyryl-para-aminophenol from phenyl n-butyrate or phenol and n-butyric acid.

We claim:

1. A process comprising contacting a hydroxy aromatic ketone with a hydroxylamine salt and a base to form the ketoxime of said ketone, and contacting said ketoxime with a Beckmann rearrangement catalyst to form an N-acyl-hydroxy aromatic amine.

2. The process of claim 1 wherein said hydroxy aromatic ketone is 4-hydroxyacetophenone, said ketoxime is 4-hydroxyacetophenone oxime, and said N-acyl-hydroxy aromatic amine is N-acetyl-para-aminophenol.

3. A process comprising contacting an ester of a phenolic compound and a carboxylic acid with a Fries rearrangement catalyst to form a hydroxy aromatic ketone, contacting said ketone with a hydroxylamine salt and a base to form a ketoxime of said ketone, and contacting said ketoxime with an acid to form an N-acyl-hydroxy aromatic amine.

4. The process comprising contacting a phenolic compound and an acylating agent with a Friedel-Crafts catalyst to form a hydroxy aromatic ketone, contacting said ketone with a hydroxylamine salt and a base to form a ketoxime of said ketone, and contacting said ketoxime with a Beckmann rearrangement catalyst to form an N-acyl-hydroxy aromatic amine.

5. The process of claim 3 wherein said Fries rearrangement catalyst is hydrogen fluoride.

6. The process of claim 4 wherein said Friedel-Crafts catalyst is hydrogen fluoride.

* * * * *

REEXAMINATION CERTIFICATE (1237th)
United States Patent [19]
Davenport et al.

[11] B1 4,524,217

[45] Certificate Issued   Apr. 3, 1990

[54] PROCESS FOR PRODUCING N-ACYL-HYDROXY AROMATIC AMINES

[75] Inventors: Kenneth G. Davenport; Charles B. Hilton, both of Corpus Christi, Tex.

[73] Assignee: Celanese Corporation, New York, N.Y.

Reexamination Request:
No. 90/001,200, Mar. 20, 1987

Reexamination Certificate for:
Patent No.: 4,524,217
Issued: Jun. 18, 1985
Appl. No.: 618,659
Filed: Jun. 8, 1984

[51] Int. Cl.$^4$ .............. C07C 103/12; C07C 103/22
[52] U.S. Cl. .................................................. 564/223
[58] Field of Search ...................................... 564/223

[56] References Cited

U.S. PATENT DOCUMENTS

4,560,789  12/1985  Davenport et al. ............ 564/223 X
4,568,763   2/1986  Davenport et al. ............ 564/223 X

OTHER PUBLICATIONS

Fieser et al. (Fieser), *Organic Chemistry*, Third Edition, Reinhold Publishing Corporation, New York, p. 566 (1956).
Stephen et al, J. Chem. Soc., pp. 886–895 (1931).
Stephen et al, J. Chem. Soc., pp. 980–985 (1956).
Donaruma et al, Organic Reactions, vol. 11, pp. 1–156 (1960).
The Chemistry of the Carbon–Nitrogen Double Bond, pp. 408–461, edited by Patai,' Interscience Publishers (1970).
Butler et al, Journal of Chemical Research (S), 1983, pp. 18–19.
Gregory et al, J. Chem. Soc. (B), 1970, pp. 338–346.
Hauser et al, J. Organic Chemistry, vol. 20, 1955, pp. 1482–1490.
Pearson et al, J. Organic Chemistry, vol. 17, 1952, pp. 1511–1518.
Jones, Chem. Reviews, vol. 35, 1974, pp. 334–350.
Fieser and Fieser, Organic Chemistry (Second Edition), D.C., Heath and Company, 1950, p. 743.
Gurav et al., Marathwada University Journal, *Acta. Chim. Indica*, 4(1):24–6 (1978).
Horning and Stromberg, *J. Am. Chem. Soc.*, 74:2680–81 (1952).
Simons et al., *J.A.C.S.*, 62:485–486 (1940).
Dann and Mylius, *Annalen der Chemie*, 587 Band, 1–15 (W. Germany, 1954)–English translation provided.

*Primary Examiner*—Charles F. Warren

[57] ABSTRACT

N-acyl-hydroxy aromatic amines, e.g. N-acetyl-para-aminophenol (APAP), are prepared by reacting a hydroxy aromatic ketone, e.g. 4-hydroxyacetophenone, with a hydroxylamine salt and a base to obtain the ketoxime of the ketone, e.g. 4-hydroxyacetophenone oxime, and then subjecting the ketoxime to a Beckmann rearrangement in the presence of a catalyst to form the N-acyl-hydroxy aromatic amine.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *